United States Patent [19]
Wong

[11] Patent Number: 5,622,938
[45] Date of Patent: Apr. 22, 1997

[54] SUGAR BASE SURFACTANT FOR NANOCRYSTALS

[75] Inventor: Sui-Ming Wong, Collegeville, Pa.

[73] Assignee: Nano Systems L.L.C., Collegeville, Pa.

[21] Appl. No.: 444,796

[22] Filed: May 19, 1995

Related U.S. Application Data

[63] Continuation-in-part of Ser. No. 386,026, Feb. 9, 1995, abandoned.

[51] Int. Cl.$^6$ .............................. A01N 43/04; A61K 31/70
[52] U.S. Cl. ..................... 514/35; 424/1.29; 424/490; 424/493; 424/499; 424/9.45
[58] Field of Search ............................... 514/35; 424/189, 424/490, 493, 499, 1.29

[56] References Cited

U.S. PATENT DOCUMENTS

| | | | |
|---|---|---|---|
| 4,107,288 | 8/1978 | Oppenheim et al. | 424/22 |
| 4,540,602 | 9/1985 | Motoyama et al. | 427/213.31 |
| 5,118,528 | 6/1992 | Fessi et al. | 427/213.36 |
| 5,145,684 | 9/1992 | Liversidge et al. | 424/489 |
| 5,403,922 | 4/1995 | Garelli-Calvet et al. | 536/1.11 |

OTHER PUBLICATIONS

Lachman, et al., The Theory and Practice of Industrial Pharmacy, Chapter 2, "Milling", p. 45, (1986).

*Primary Examiner*—Nathan M. Nutter
*Attorney, Agent, or Firm*—Rudman & Balogh

[57] ABSTRACT

Dispersible particles consisting essentially of a crystalline drug substance having a surface modifier having the formula:

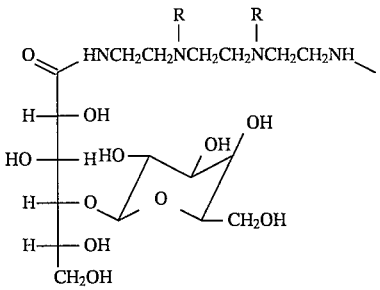

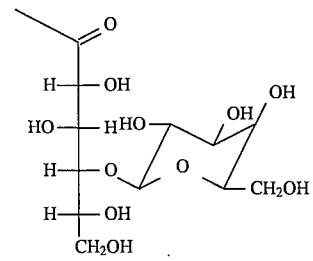

wherein R is phenyl-$(CH_2)_{10}CO$ or $C_{12}H_{25}NHCO$ adsorbed on the surface thereof in an amount sufficient to maintain an effective average particle size of less than about 400 nm, methods for the preparation of such particles and dispersions containing the particles. Pharmaceutical compositions containing the particles exhibit unexpected bioavailability and are useful in methods of treating mammals.

20 Claims, No Drawings

SUGAR BASE SURFACTANT FOR NANOCRYSTALS

CROSS-REFERENCE TO RELATED APPLICATIONS

This is a continuation-in-part of application Ser. No. 08/386,026, filed 09 Feb. 1995 and now abandoned, entitled, "SUGAR BASE SURFACTANT FOR NANOCRYSTALS" by Sui-Ming Wong.

FIELD OF THE INVENTION

This invention relates to drug particles, methods for the preparation thereof and dispersions containing the particles. This invention further relates to the use of such particles in pharmaceutical compositions and methods of treating mammals.

BACKGROUND OF THE INVENTION

Bioavailability is the degree to which a drug becomes available to the target tissue after administration. Many factors can affect bioavailability including the dosage form and various properties, e.g., dissolution rate of the drug. Poor bioavailability is a significant problem encountered in the development of pharmaceutical compositions, particularly those containing an active ingredient that is poorly soluble in water. Poorly water soluble drugs, i.e., those having a solubility less than about 10 mg/ml, tend to be eliminated from the gastrointestinal tract before being absorbed into the circulation. Moreover, poorly water soluble drugs tend to be unsafe for intravenous administration techniques, which are used primarily in conjunction with fully soluble drug substances.

It is known that the rate of dissolution of a particulate drug can increase with increasing surface area, i.e., decreasing particle size. Consequently, methods of making finely divided drugs have been studied and efforts have been made to control the size and size range of drug particles in pharmaceutical compositions. For example, dry milling techniques have been used to reduce particle size and hence influence drug absorption. However, in conventional dry milling, as discussed by Lachman, et al., *The Theory and Practice of Industrial Pharmacy*, Chapter 2, "Milling", p 45 (1986) the limit of fineness is reached in the region of 100 microns (100,000 nm) when material cakes on the milling chamber. Lachman, et al. note that wet grinding is beneficial in further reducing particle size, but that flocculation restricts the lower particle size limit to approximately 10 microns (10,000 nm). However, there tends to be a bias in the pharmaceutical art against wet milling due to concerns associated with contamination. Commercial airjet milling techniques have provided particles ranging in average particle size from as low as about 1 to 50 µm (1,000–50,000 nm).

Other techniques for preparing pharmaceutical compositions include loading drugs into liposomes or polymers, e.g., during emulsion polymerization. However, such techniques have problems and limitations. For example, a lipid soluble drug is often required in preparing suitable liposomes. Further, unacceptably large amounts of the liposome or polymer are often required to prepare unit drug doses. Further still, techniques for preparing such pharmaceutical compositions tend to be complex. A principal technical difficulty encountered with emulsion polymerization is the removal of contaminants, such as unreacted monomer or initiator, which can be toxic, at the end of the manufacturing process.

U.S. Pat. No. 4,540,602 (Motoyama et al.) discloses a solid drug pulverized in an aqueous solution of a water-soluble high molecular substance using a wet grinding machine. However, Motoyama et al. teach that as a result of such wet grinding, the drug is formed into finely divided particles ranging from 0.5 µm (500 nm) or less to 5 µm (5,000 nm) in diameter.

EPO 275,796 describes the production of colloidally dispersible systems comprising a substance in the form of spherical particles smaller than 500 nm. However, the method involves a precipitation effected by mixing a solution of the substance and a miscible non-solvent for the substance and results in the formation of non-crystalline nonoparticles. Furthermore, precipitation techniques for preparing particles tend to provide particles contaminated with solvents. Such solvents are often toxic and can be very difficult, if not impossible, to adequately remove to pharmaceutically acceptable levels to be practical.

U.S. Pat. No. 4,107,288 describes particles in the size range from 10 to 1,000 nm containing a biologically or pharmacodynamically active material. However, the particles comprise a crosslinked matrix of macromolecules having the active material supported on or incorporated into the matrix.

U.S. Pat. No. 5,145,684 describes unique nanoparticles comprising a crystal-drug substance having a surface modifier adsorbed on the surface thereof in an amount sufficient to maintain an effective average particle size of less than about 400 nm, methods for the preparation of such particles and dispersions containing the particles. Pharmaceutical compositions containing the particles exhibit unexpected bioavailability and are useful in methods of treating mammals.

It would be desirable to provide even more stable dispersible drug particles in the submicron size range which can be readily prepared and which do not appreciably flocculate or agglomerate due to interparticle attractive forces and do not require the presence of a crosslinked matrix. Moreover, it would be highly desirable to provide pharmaceutical compositions having enhanced bioavailability over those described in U.S. Pat. No. 5,145,684.

SUMMARY OF THE INVENTION

We have discovered stable, dispersible drug nanoparticles and a method for preparing such particles by wet milling in the presence of grinding media in conjunction with a specific surface modifier. The particles can be formulated into pharmaceutical compositions exhibiting remarkably high bioavailability.

More specifically, in accordance with this invention, there are provided particles consisting essentially of a crystalline drug substance having a surface modifier adsorbed on the surface thereof in an amount sufficient to maintain an effective average particle size of less than about 400 nm.

This invention also provides a stable dispersion consisting essentially of a liquid dispersion medium and the above-described particles dispersed therein.

In another embodiment of the invention, there is provided a method of preparing the above-described particles comprising the steps of dispersing a drug substance in a liquid dispersion medium and applying mechanical means in the presence of grinding media to reduce the particle size of the drug substance to an effective average particle size of less than about 400 nm. The particles can be reduced in size in the presence of a surface modifier. Alternatively, the particles can be contacted with the surface modifier after attrition.

In a particularly valuable and important embodiment of the invention, there is provided a pharmaceutical composition comprising the above-described particles and a pharmaceutically acceptable carrier therefor. Such pharmaceutical composition is useful in a method of treating mammals.

It is an advantageous feature that a wide variety of surface modified drug nanoparticles free of unacceptable contamination can be prepared in accordance with this invention.

It is another advantageous feature of this invention that there is provided a simple and convenient method for preparing drug nanoparticles by wet milling in conjunction with the surface modifier.

Another particularly advantageous feature of this invention is that pharmaceutical compositions are provided exhibiting unexpectedly high bioavailability.

Still another advantageous feature of this invention is that pharmaceutical compositions containing poorly water soluble drug substances are provided which are suitable for intravenous administration techniques.

Other advantageous features will become readily apparent upon reference to the following Description of Preferred Embodiments.

DESCRIPTION OF PREFERRED EMBODIMENTS

This invention is based on the discovery that drug particles having an extremely small effective average particle size can be prepared by wet milling in the presence of grinding media in conjunction with a specific surface modifier, and that such particles are stable and do not appreciably flocculate or agglomerate due to interparticle attractive forces and can be formulated into pharmaceutical compositions exhibiting unexpectedly high bioavailability. While the invention is described herein primarily in connection with its preferred utility, i.e., with respect to nanoparticulate drug substances for use in pharmaceutical compositions, it is also believed to be useful in other applications such as the formulation of particulate cosmetic compositions and the preparation of particulate dispersions for use in image and magnetic recording elements.

The particles of this invention comprise a drug substance. The drug substance exists as a discrete, crystalline phase. The crystalline phase differs from a non-crystalline or amorphous phase which results from precipitation techniques, such as described in EPO 275,796 cited above.

The invention can be practiced with a wide variety of drug substances. The drug substance preferably is present in an essentially pure form. The drug substance must be poorly soluble and dispersible in at least one liquid medium. By "poorly soluble" it is meant that the drug substance has a solubility in the liquid dispersion medium of less than about 10 mg/ml, and preferably of less than about 1 mg/ml. A preferred liquid dispersion medium is water. However, the invention can be practiced with other liquid media in which a drug substance is poorly soluble and dispersible including, for example, aqueous salt solutions, safflower oil and solvents such as ethanol, t-butanol, hexane and glycol. The pH of the aqueous dispersion media can be adjusted by techniques known in the art.

Suitable drug substances can be selected from a variety of known classes of drugs including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immuriological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators and xanthines. Preferred drug substances include those intended for oral administration and intravenous administration. A description of these classes of drugs and a listing of species within each class can be found in Martindale, *The Extra Pharmacopoeia,* Twenty-ninth Edition, The Pharmaceutical Press, London, 1989, the disclosure of which is hereby incorporated by reference in its entirety. The drug substances are commercially available and/or can be prepared by techniques known in the art.

Representative illustrative species of drug substances useful in the practice of this invention include:

17-pregno-2,4-dien-20-yno-[2,3-d]-isoxazol-17-ol (Danazol);

5,17,-1'-(methylsulfonyl)-1'H-pregn-20-yno [3,2-c]-pyrazol-17-ol (Steroid A);

piposulfam;

piposulfan;

camptothecin; and ethyl-3,5-diacetoamido-2,4,6-triiodobenzoate

In particularly preferred embodiments of the invention, the drug substance is a diagnostic agent surface modifier having the structure:

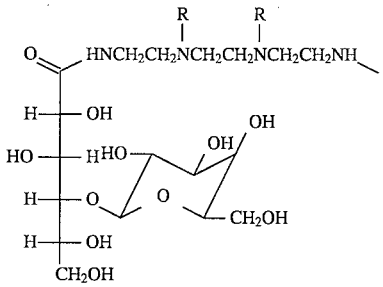

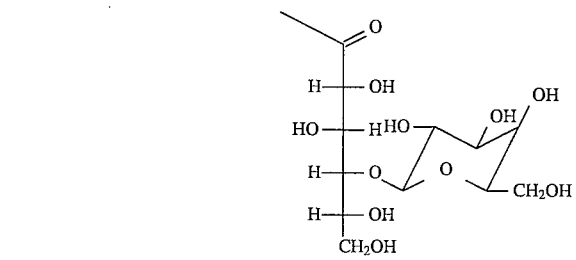

wherein R is $Ph(CH_2)_{10}CO$ wherein Ph is phenyl or $C_{12}H_{25}NHCO$ adsorbed on the surface thereof.

The particular surface modifier provides the nanodispersible particles with unexpectedly reduced mean particle size and limiting the particle size growth during terminal sterlization of the nanocrystal formulations.

The surface modifier of this invention is the discovery of Ian Newington and Katie Adams.

The surface modifier is adsorbed on the surface of the drug substance in an amount sufficient to maintain an effective average particle size of less than about 400 nm. The surface modifier does not chemically react with the drug substance or itself. Furthermore, the individually adsorbed molecules of the surface modifier are essentially free of intermolecular crosslinkages.

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of less than about 400 nm" it is meant that at least 90% of the particles have a weight average particle size of less than about 400 nm when measured by the above-noted techniques. In preferred embodiments of the invention, the effective average particle size is less than about 250 nm. In some embodiments of the invention, an effective average particle size of less than about 100 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

The particles of this invention can be prepared in a method comprising the steps of dispersing a drug substance in a liquid dispersion medium and applying mechanical means in the presence of grinding media to reduce the particle size of the drug substance to an effective average particle size of less than about 400 nm. The particles can be reduced in size in the presence of a surface modifier. Alternatively, the particles can be contacted with a surface modifier after attrition.

A general procedure for preparing the particles of this invention is set forth below. The drug substance selected is obtained commercially and/or prepared by techniques known in the art in a conventional coarse form. It is preferred, but not essential, that the particle size of the coarse drug substance selected be less than about 100 μm as determined by sieve analysis. If the coarse particle size of the drug substance is greater than about 100 μm, then it is preferred that the particles of the drug substance be reduced in size to less than 100 μm using a conventional milling method such as airier or fragmentation milling.

The coarse drug substance selected can then be added to a liquid medium in which it is essentially insoluble to form a premix. The concentration of the drug substance in the liquid medium can vary from about 0.1–60%, and preferably is from 5–30% (w/w). It is preferred, but not essential, that the surface modifier be present in the premix. The concentration of the surface modifier can vary from about 0.1 to about 90%, and preferably is 1–75%, more preferably 20–60%, by weight based on the total combined weight of the drug substance and surface modifier. The apparent viscosity of the premix suspension is preferably less than about 1000 centipoise The premix can be used directly by subjecting it to mechanical means to reduce the average particle size in the dispersion to less than 400 nm. It is preferred that the premix be used directly when a ball mill is used for attrition. Alternatively, the drug substance and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

The mechanical means applied to reduce the particle size of the drug substance conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the intended result, i.e., the desired reduction in particle size.

For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. We have found that zirconium oxide, such as 95% ZrO stabilized with magnesia, zirconium silicate, and glass grinding media provide particles having levels of contamination which are believed to be acceptable for the preparation of pharmaceutical compositions. However, other media, such as stainless steel, titania, alumina, and 95% ZrO stabilized with yttrium, are expected to be useful. Preferred media have a density greater than about 3 g/cm$^3$.

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill.

The particles must be reduced in size at a temperature which does not significantly degrade the drug substance. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

The surface modifier, if it was not present in the premix, must be added to the dispersion after attrition in an amount as described for the premix above. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of drug substance and surface modifier can vary widely and the optimal amount of the surface modifier can depend, for example, upon the particular drug substance and surface modifier selected, the critical micelle concentration of the surface modifier if it forms micelles, etc. The surface modifier preferably is present in an amount of about 0.1–10 mg per square meter surface area of the drug substance. The surface modifier can be present in an amount of 0.1–90%, preferably 20–60% by weight based on the total weight of the dry particle.

The resulting dispersion of this invention is stable and consists of the liquid dispersion medium and the above-described particles. The dispersion of surface modified drug nanoparticles can be spray coated onto sugar spheres or onto a pharmaceutical excipient in a fluid-bed spray coater by techniques well known in the art.

Pharmaceutical compositions according to this invention include the particles described above and a pharmaceutically acceptable carrier therefor. Suitable pharmaceutically acceptable carriers are well known to those skilled in the art. These include non-toxic physiologically acceptable carriers, adjuvants or vehicles for parenteral injection, for oral administration in solid or liquid form, for rectal administration, and the like. A method of treating a mammal in accordance with this invention comprises the step of administering to the mammal in need of treatment an effective amount of the above-described pharmaceutical composition. The selected dosage level of the drug substance for treatment is effective to obtain a desired therapeutic response for a particular composition and method of administration. The selected dosage level therefore, depends upon the particular drug substance, the desired therapeutic effect, on the route of administration, on the desired duration of treatment and other factors. As noted, it is a particularly advantageous feature that the pharmaceutical compositions of this invention exhibit unexpectedly high bioavailability as illustrated in the examples which follow. Furthermore, it is contemplated that the drug particles of this invention provide more rapid onset of drug action and decreased gastrointestinal irritancy.

It is contemplated that the pharmaceutical compositions of this invention will be particularly useful in oral and parenteral, including intravenous, administration applications. It is expected that poorly water soluble drug substances, which prior to this invention, could not have been administered intravenously, may be administered safely in accordance with this invention. Additionally, drug substances which could not have been administered orally due to poor bioavailability may be effectively administered in accordance with this invention.

The following Examples further illustrate the invention.

EXAMPLE 1

Preparation of SA90HEA

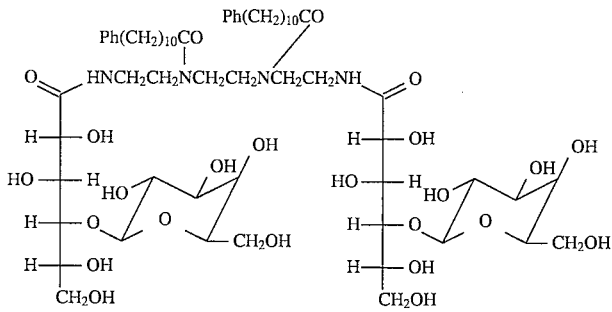

To a solution of lactobionic acid (17.92 g, 50 mmol, 2 equivs. Aldrich 97%) in DMF (Dimethylformamide, 100 ml, dried over 4A° molecular sieves). The reaction mixture was stirred at 70° C. under argon for 18 hours. The solution was cooled to 50° C. The resulting product was N, N10-triethylenetetramine-bislactobionamide. N4,N7-diphenylundecanoyl-N1,N10-triethylenetetramine-bislactobionamide-SA90HEA as prepared by dissolving phenylundecanoic acid (13.12 g, 50 mmol, 2 equivs. Eastman Chemicals 99%) in diethyl ether (40 ml) and cooling in an ice-bath. Triethylamine (5.06 g, 500 mmol, 2 equivs, Prolabo) was added followed by ethyl chloroformate (5.53 g, 51 mmol, 2.04 equivs. Lancaster), the mixture was stirred well. After 30 mins. filtered into a solution of N1, N10-triethylenetetraminebislactobionamide (20.67 g, 25 mmol, 1 equiv) in DMF (100 ml, dried over 4A° molecular sieves) and washed well with diethyl ether. The mixture was stirred at 50° C. for 6 hours. After cooling to room temperature, the solvent was evaporated under reduced pressure to leave an orange crystalline material, which was washed with diethyl ether, collected by Buchner filtration and briefly dried under high vacuum to leave an orange powder (30.72 g, 93% yield). A portion of this material (13 g) was then dissolved in distilled water (40 ml) and stirred with Amberlite IRA-420(OH) resin (BDH) at pH=10 for 40 mins. The resin was removed by buchner filtration and the product was obtained after freeze drying overnight which removed the water. SA90HEA was obtained as a fine pale yellow powder (7.47 g, 57% yield).

EXAMPLE 2

Preparation of SA90HEG

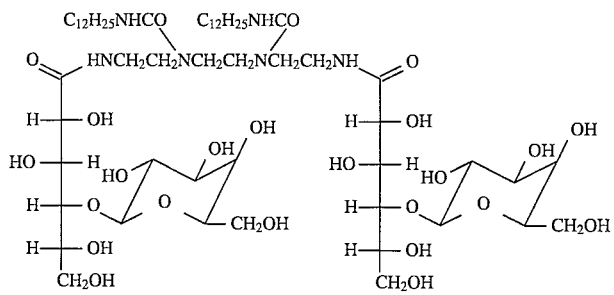

N4,N7-didodecylisocyano-N1,N10-triethylenetetramine-bislactobionamide - SA90HEG was prepared by adding Dodecyl isocyanate (10.57 g, 50 mmol, 2 equivs. Eastman Chemicals 95%) to a solution of N1, N10-triethlenetetraminebislactobionamide (20.67 g, 25 mmol, 1 equiv) in DMF (100 ml, dried over 4A° molecular sieves). The reaction mixture was heated at 50° C. under argon for 7 hours. After cooling to room temperature, the solvent was evaporated under reduced pressure to leave a yellow crystalline material, which was washed with diethyl ether, collected by Buchner filtration and briefly dried under high vacuum to leave a yellow powder (29.15 g, 93% yield). A portion of this material (16 ) was then dissolved in distilled water (50 ml) and stirred with Amberlite IRA-420(OH) resin (BDH) at pH=10 for 40 mins. The resin was removed by Buchner filtration and the product was obtained after freeze drying overnight which removed the water. SA90HEG was obtained as a fine cream powder (11.19 g, 70% yield).

EXAMPLES 3–6

The following formulations were prepared at 15% diagnostic agent and 4% surfactant (w/v). A 6% stock solution was prepared by dissolving 600 mg of SA90HEA and SA90HEG in 10 ml deionized water. To each 15 ml amber colored bottle, 7.5 ml of 6% stock surfactant solution and 0.994 ml deionized water were addded. The sample bottle was sealed and placed on a roller mill running at 160 rpm for 7 days. At day 7, aliquot f samples were diluted 100 fold with deionized water for particle size measurement by Photon Correlation Spectroscopy (Microtrac).

For terminal sterlization, 1 ml of nanocrystal formulation prepared above was pipetted into a 2 ml serum vial. After sealing with rubber septum and aluminum cap, the samples were subjected to autoclave at 121° C. for 20 min. On cooling to room temperature, aliquots of samples were retrieved from the vial and diluted 100 fold with deionized water for particle size measurement by Photon Correlation Spectroscopy (Microtract).

| | | | Mean Particle Size (nm) | |
|---|---|---|---|---|
| Example | Core | Surfactant | Before Auto | After Auto |
| 3 | Compound A | SA90HEA | 55 | 125 |
| 4 | Compound A | SA90HEG | 87 | 194 |
| A | Compound A | F108 | 130 | >500 |
| B | Compound A | T908 | 241 | >500 |
| 5 | Compound B | SA90HEA | 77 | |
| 6 | Compound B | SA90HEG | 71 | |

Compound A = WIN 8883

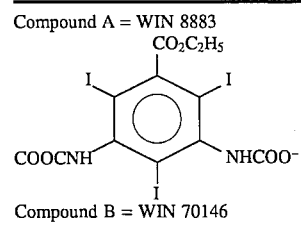

Compound B = WIN 70146

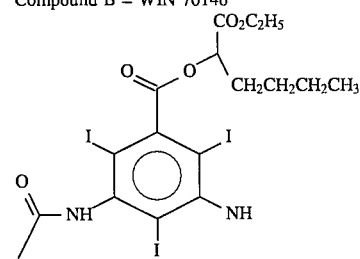

Comparing to the commercially available copolymeric surfactants under identical milling and autoclave conditions, this data demonstrates that the sugar surfactants, SA90HEA and SA90HEG, resulted in unexpectedly reduced mean particle size and limited the particle size growth during terminal sterilization of the nanocrystal formulations.

In addition, tail vein injection of a 4% solution of SA90HEA and SA90HEG at 30 ml/Kg was well tolerated by mice. SA90HEA and SA90HEG were tested in a smudge cell evaluation. Both SA90HEG and SA90HEA were devoid of smudge cell effect.

SA90HEA and SA90HEG also significantly inhibited the uptake of polystyrene particle by macrophages.

The invention has been described in detail with particular reference to preferred embodiments thereof, but it will be understood that variations and modifications can be effected within the spirit and scope of the invention.

What is claimed is:

1. Particles consisting essentially of a crystalline drug substance having a surface modifier having the structure:

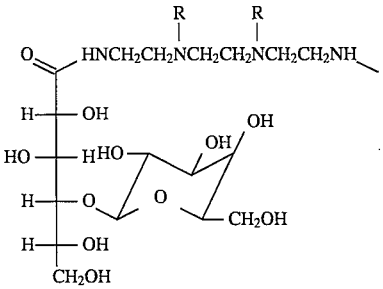

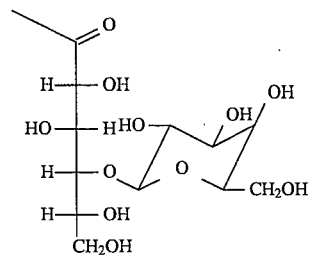

wherein R is $Ph(CH_2)_{10}CO$ or $C_{12}H_{25}NHCO$ adsorbed on the surface thereof in an amount sufficient to maintain an effective average particle size of less than about 400 nm.

2. The particles of claim 1 having an effective average particle size of less than 250 nm.

3. The particles of claim 1 having an effective average particle size of less than 100 nm.

4. The particles of claim 1 wherein said drug substance is selected from analgesics, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, contrast media, corticosteroids, cough suppressants, diagnostic agents, diagnostic imaging agents, diuretics, dopaminergics, haemostatics, immuriological agents, lipid regulating agents, muscle relaxants, parasympathomimetics, parathyroid calcitonin, prostaglandins, radio-pharmaceuticals, sex hormones, anti-allergic agents, stimulants, sympathomimetics, thyroid agents, vasodilators and xanthines.

5. The particles of claim 1 wherein the drug substance is a diagnostic agent.

6. The particles of claim 5 wherein the drug substance is

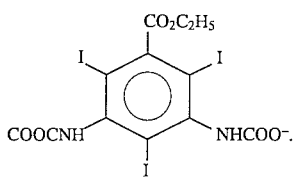

7. The particles of claim 5 wherein the drug substance is

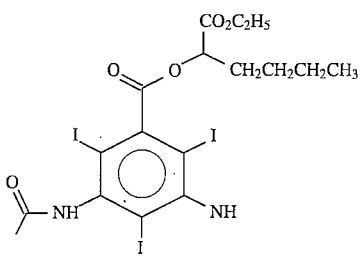

8. The particles of claim 1 wherein the surface modifier is

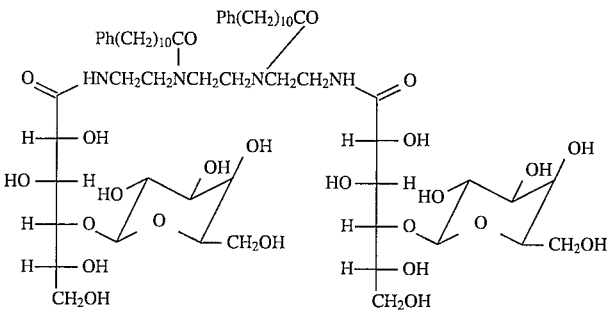

9. The particles of claim 1 wherein the surface modifier is

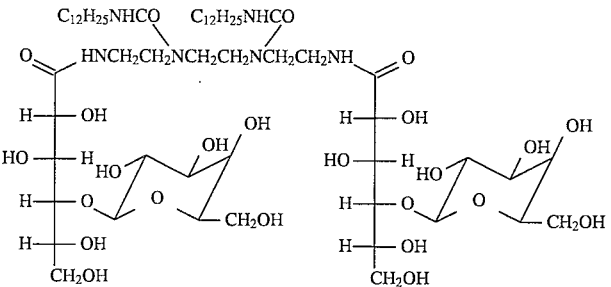

10. Particles consisting essentially of a discrete phase of 5,17,-1'-(methylsulfonyl)-1'H-pregn-20-yno-[3,2-c]-pyrazol-17-ol having an ethylene oxide propylene-oxide block copolymer adsorbed on the surface thereof in an amount sufficient to maintain an effective average particle size of less than about 400 nm.

11. A stable dispersion consisting essentially of a liquid dispersion medium and the particles of claim 1.

12. The dispersion of claim 10 wherein said dispersion medium is water.

13. The dispersion of claim 10 wherein said dispersion medium is selected from the group consisting of safflower oil, ethanol, t-butanol, hexane and glycol.

14. A pharmaceutical composition comprising the particles of claim 1 and a pharmaceutically acceptable carrier therefor.

15. A method of treating a mammal comprising the step of administering to the mammal an effective amount of the pharmaceutical composition of claim 13.

16. Particles of claim 1 in a stable dispersion containing with a liquid dispersion medium.

17. Particles of claims 1 in a stable aqueous dispersion.

18. Particles of claim 1 in a stable dispersion containing with a liquid dispersion medium, wherein the medium is safflower oil, ethanol, t-butanol, hexane or glycol.

19. Particles of claim 1 in a pharmaceutical composition containing a pharmaceutical acceptable carrier for the particles.

20. Particles of claim 1 used in a method of treating a mammal wherein the particles are administered to the mammal.

* * * * *